United States Patent [19]

Higuchi et al.

[11] 4,052,505

[45] * Oct. 4, 1977

[54] OCULAR THERAPEUTIC SYSTEM MANUFACTURED FROM COPOLYMER

[75] Inventors: Takeru Higuchi, Lawrence, Kans.; Anwar Hussain, Lexington, Ky.

[73] Assignee: Alza Corporation, Palo Alto, Calif.

[*] Notice: The portion of the term of this patent subsequent to Sept. 9, 1992, has been disclaimed.

[21] Appl. No.: 705,479

[22] Filed: July 15, 1976

Related U.S. Application Data

[60] Continuation of Ser. No. 582,353, May 5, 1975, which is a division of Ser. No. 281,446, Aug. 17, 1972, Pat. No. 3,903,880, which is a continuation-in-part of Ser. No. 80,531, Oct. 14, 1970, abandoned.

[51] Int. Cl.² ........................... A61K 9/00; A61K 9/22
[52] U.S. Cl. ...................................... 424/14; 128/260; 424/16; 424/19; 424/22; 424/28

[58] Field of Search .............. 128/260; 424/14, 19-22, 424/28

[56] References Cited

U.S. PATENT DOCUMENTS

| 3,710,795 | 1/1973 | Higuchi et al. | 128/260 |
| 3,854,480 | 12/1974 | Zaffaroni | 128/260 |

*Primary Examiner*—Shep K. Rose
*Attorney, Agent, or Firm*—Paul L. Sabatine; Steven D. Goldby

[57] ABSTRACT

Drug-delivery device for releasing a drug at a continuous and controlled rate for a prolonged period of time is comprised of a shaped body of polymeric material containing a pharmaceutically acceptable drug and permeable to passage of the drug by diffusion. The polymeric material is an ethylene-vinyl acetate copolymer having a vinyl acetate content of about 4 to 80% by weight and a melt index of about 0.1 to 1000 grams per 10 minutes.

19 Claims, 5 Drawing Figures

U.S. Patent    Oct. 4, 1977    4,052,505
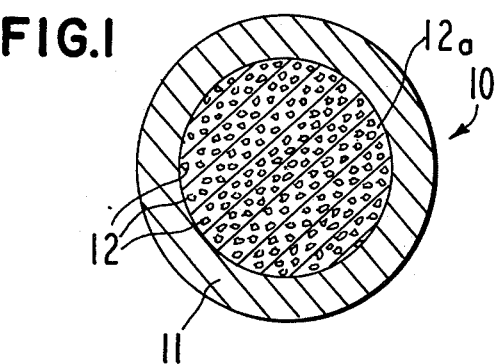
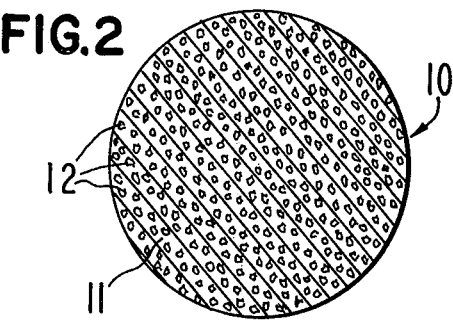
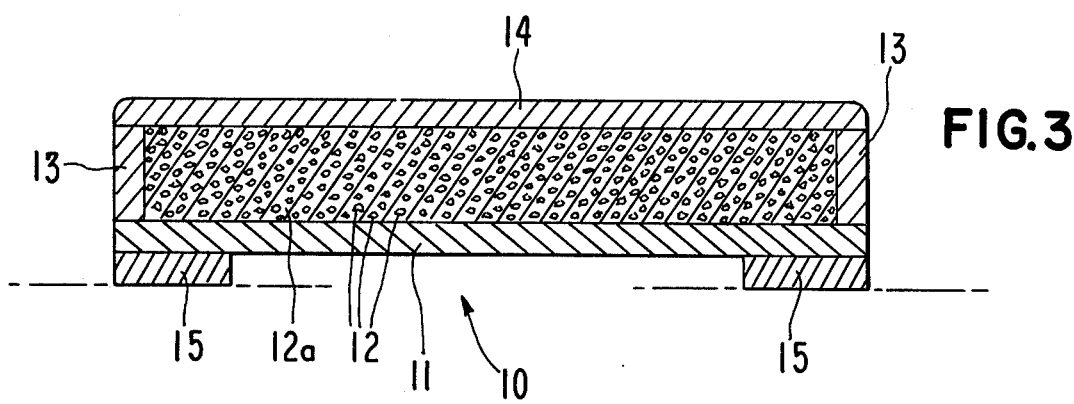
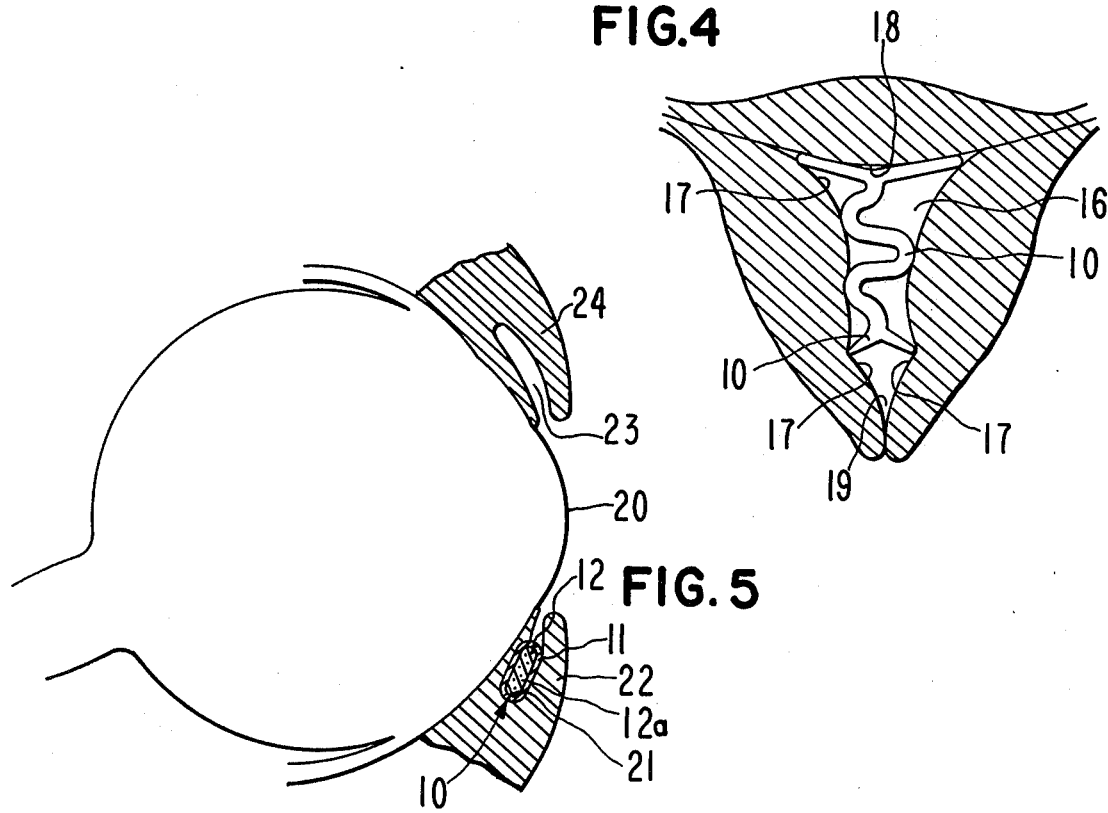

OCULAR THERAPEUTIC SYSTEM MANUFACTURED FROM COPOLYMER

CROSS-REFERENCE TO RELATED APPLICATIONS

This application is a continuation of U.S. patent application Ser. No. 582,353 filed on May 5, 1975 which application is a division of U.S. patent application Ser. No. 281,446 filed on Aug. 17, 1972, now U.S. Pat. No. 3,903,880, which application is a continuation-in-part of U.S. patent application Ser. No. 80,531, filed on Oct. 14, 1970 and now abandoned. These applications are assigned to the same assignee of this application and benefit of their filing dates is claimed.

BACKGROUND OF THE INVENTION

This invention relates to a novel and useful drug-delivery device for releasing a pharmaceutically acceptable drug at a controlled and continuous rate for a prolonged period of time to produce a physiological or pharmacological effect. The drug delivery device is comprised of a drug release rate controlling polymeric material surrounding at least a part of the drug or the material contains the drug therein. The material is permeable to the passage of drug by diffusion.

Often, in therapeutic, medical and veterinary programs, it is desirable and important to provide for the slow release of a drug to the body at a controlled rate over a prolonged period of time. In many therapeutic programs such a rate of release should be constant or have a zero order time dependence, that is, the rate of release is independent of time. For example, in contraception, it has been found that fertility can be regulated by release of progesterone to the uterus from a drug-delivery device inserted in the uterine lumen; with release of progesterone at a constant rate for a prolonged period, a convenient long term birth control procedure is provided. Similary, glaucoma can be controlled by release of pilocarpine from a thin film drug-delivery device inserted beneath the lower eyelid. Here too, the active beneficial agent should be released at a constant rate.

Different approaches have heretofore been tried to obtain a drug-delivery device for releasing drug at a conrolled rate. One approach, which has received great attention, is to mix the drug with a carrier material that is gradually broken down by body fluids, the drug being released as the carrier disintegrates. Numerous carriers have been used in such systems including waxes, oils, fats, soluble polymers and the like. While some of these systems have provided for a delayed release of the drug, constant release rate has not been obtained. One reason for this is that as the carrier disintegrates the surface area of the dosage unit decreases, concomitantly exposing increasingly smaller quantities of the carrier to the surrounding body fluids. This inherently results in a decline in the release rate over time. Moreover, there has been little success in gaining control over drug release rate by this approach.

Another approach has been to enclose the drug within a capsule having polymeric walls through which the drug can pass by diffusion. An approach of this kind is set forth in U.S. Pat. No. 3,279,996. These devices too have inherent difficulties. These prior systems have generally been based on the use of silicone rubber polymers, especially polydimethylsiloxanes, as the diffusion control membrane. In large part, these silicone polymers were selected because of their high permeability to some important drug molecules. But it has now been found that this high permeability can be a significant disadvantage which defeats the primary objective of an acceptable and useful drug-delivery device. Thus, with many important drug molecules, such as progesterone, the diffusion rate through polydimethylsiloxane membranes is very great, often greater than the rate of clearance of the diffused drug from the outer surface of the capsule. In many instances, this results in the rate limiting step being clearance of the drug from the exterior of the capsule, rather than diffusion through the capsule wall. Clearance rate within the body is difficult to control, as it is subject to frequent changes and, when it is the rate-limiting step, the objective of providing a drug-delivery device which releases drug at a constant rate over time cannot be obtained. Also, silicone rubbers have a tendency to absorb lipoidal materials from the body. When this effect occurs in vivo, the nature of the membrane changes, altering the release rate. Still another problem with the silicone rubber dosage forms is the difficulty encountered in fabrication, attributable largely to the silicone rubber itself, that is, it is not thermoplastic and accordingly it does not lend itself to the manufacture of heat selaed drug delivery devices. While the above mentioned polymer, silicone, has been found to have too high a permeability to many therapeutic drugs to lend itself to successful use as a drug release rate controlling barrier, in other instances, polymers such as poly(ethylene), which is thermoplastic and has a high degree of crystallinity, has also been found to have too high a melting point that can adversely affect the drug during fabrication of the device, and because of its crystallinity has too low a permeability to drug to be successfully used as a drug release rate barrier.

In unrelated, non-therapeutic fields, various other polymeric materials have been used for releasing active substances. For example, a closed container whose walls are comprised of ethylene vinyl acetate copolymer is described in U.S. Pat. No. 3,310,235 as seemingly suitable for releasing volatile, organic and toxic phosphorous biocides by the process of physical evaporation. With these containers, all biocide release is achieved by evaporation from the surface, and if the ingredient is not sufficiently volatile at the use temperature the container has no apparent practical value. Evaporation is preferably achieved by using a woven cloth which acts as an evaporation surface. However, release rate by evaporation is difficult to regulate and virtually impossible to control as it is subjected to uncontrollable environmental conditions, the vapor pressure of the substance, and the degree of saturation of the volatile substance in the environment. The type of clearance inherently defeats the basic purpose of providing a drug delivery device which releases a drug at a controlled rate for a prolonged period of time such as by the process of diffusion.

It is also known to the art to use polymeric materials such as ethylene-vinyl acetate copolymer in other forms and for different purposes. For example, in Great Britain Pat. No. 1,126,849 there is disclosed a cellular polymer in which open cells are purposely formed for the movement of gases into these pores. These cellular polymers are disclosed to have non-medical uses and generally these polymers do not lend themselves to use as diffusional drug devices. In U.S. Pat. No. 3,400,011 polymeric materials are mixed with waxes and used for coating ingredients that are subsequently released by the osmotic movement of external fluids into the coating causing it to rupture and release the surrounded ingredient. In U.S. Pat. No. 3,618,604 there is disclosed an ocular drug delivery device that represents a substantial improvement over previously proposed drug devices and which devices can be successfully used for their intended purpose in the management of ocular medicine. But, the use of some of the materials set forth therein, for example, partially hydrolyzed polyvinylacetate because of its gel like properties, has led to manufacturing difficulties and also has not given the desired drug release rates in many instances. Other incidental and non-therapeutic uses for vinyl acetate copolymers are disclosed in French Patent 1,489,490 as a thickner and in French Patent 1,505,267 as a non-diffusional formless base for chewing gum.

SUMMARY OF THE INVENTION

One important object of this invention is to provide a novel and useful shaped drug-delivery device for prolongedly releasing drug at a controlled rate, by providing a material that has the ability to given therapeutically operable drug release rates in vivo, while simultaneously remaining substantially free of any adverse unwanted toxic effects to the host.

Still another object of this invention is to provide a medical and veterinary useful drug-delivery device which can release drug at a rate which does no vary with time.

One further object of this invention is to provide an intrauterine, shaped memory retaining device for controlling fertility over a long period of time.

Yet a further object of this invention is to provide a drug delivery device fabricated from a material which is compatible with body tissue and exhibits a low toxicity thereto.

Still yet another object of the invention is to provide a reliable and easily used drug delivery device for continuously administered controlled quantities of drug to the body or to a drug receptor site.

Still a further and immediate object of this invention is to provide a drug delivery device for the administration of a locally acting or systemically acting drug to produce a physiologic or pharmacologic effect.

Still another object of the invention is to provide a drug delivery device made from a material that can be fabricated, e.g., heat sealed, without substantially adversely effecting the properties of the drug contained therein.

Yet a further object of the invention is to provide a drug delivery device formed of a drug release rate controlling material permeable to the passage of drug by diffusion which process is the drug release rate controlling for the drug delivery device.

In accomplishing the objects of this invention, one feature resides in a drug-delivery device for releasing drugs over a prolonged period of time comprising a drug reservoir and a polymeric barrier through which the drug passed by diffusion. The polymeric barrier is an ethylene-vinyl acetate copolymer having a vinyl acetate content of about 4 to 80% by weight and a melt index of about 0.1 to 1000 grams per ten minutes.

Another feature of this invention resides in a drug dosage form for releasing drug at a predetermined rate over a prolonged period of time comprising a body of polymeric material containing a drug, the polymeric body being permeable to passage of the drug by diffusion and being comprised of an ethylene-vinyl acetate copolymer having a vinyl acetate content of about 4 to 80% by weight and a melt index of about 0.1 to 1000 grams per ten minutes.

Still another feature of this invention resides in a new and useful drug delivery device for insertion in the uterine lumen through the cervix, the device comprising a biologically acceptable body of polymeric material containing a progestational agent, the polymeric body being permeable to passage of the progestational agent at a fertility controlling rate by diffusion and being comprised of an ethylene-vinyl acetate copolymer having a vinyl acetate content of about 4 to 80% by weight and a melt index of about 0.1 to 1000 grams per ten minutes.

Yet a further feature of this invention resides in an eye medication dispensing device which is a flexible body of an ethylene-vinyl acetate copolymer having a vinyl acetate content of about 4 to 80% by weight and a melt index of about 0.1 to 1000 grams per ten minutes. The device contains an ophthalmic drug which is dispensed to the eye by diffusion through the copolymer. The device is adapted for insertion in the cul-de-sac of the conjunctiva between the sclera of the eyeball and the lid, to be held in place against the eyeball by the pressure of the lid.

Yet a further feature of this invention resides in a drug dispensing device which is comprised of a flexible body of an ethylene vinyl acetate copolymer having a vinyl acetate content of about 4 to 80% by weight and a melt index of about 0.1 to 1000 grams per ten minutes. The device contains a drug which is released from the device by diffusion through the copolymer to the vagina, bladder or other body cavity.

Other objects, features and advantages of this invention will become more apparent to those skilled in the art from the following detailed description of the invention, taken in conjunction with the drawings, and the accompanying claims.

BRIEF DESCRIPTION OF THE DRAWINGS

In the drawings, which are not drawn to scale, but rather are set forth to illustrate various embodiments of the invention and wherein like reference numerals designate like parts, the drawings are as follows:

FIG. 1 is a side cross-sectional view of a drug-delivery device of the invention;

FIG. 2 is a side cross-sectional view of another embodiment of the drug-delivery device of the invention;

FIG. 3 is a side cross-sectional view of still another embodiment of the invention in the form of an adhesive patch;

FIG. 4 is a front view, partially in cross-section, of the drug-delivery device of the invention in the form of a drug dispensing intrauterine device; and FIG. 5 is a side view, partially in cross-section, of the device of the invention in the form of an eye medication dispensing device.

DETAILED DESCRIPTION OF THE INVENTION

In accordance with this invention, it has now been unexpectedly found that ethylene-vinyl acetate copolymers can be successfully manufactured into novel and useful drug delivery devices and can therefore be used for the controlled release of drugs by diffusion.

As illustrated in FIG. 1, the novel and useful drug-delivery device 10 of the invention can have a wall 11 fabricated of ethylene-vinyl acetate copolymer enclosing a reservoir 12a containing a drug 12. Drug 12 is one capable of diffusing through ethylene-vinyl acetate copolymer walls 11. Alternatively, as illustrated in FIG. 2, the drug-delivery device 10 can be comprised of a solid matrix 11 of ethylene-vinyl acetate copolymer, which also serves as a drug reservoir, having drug 12 distributed therethrough.

Essential to this invention is the use of an ethylene-vinyl acetate copolymer as the rate limiting barrier for the controlled release of drugs by diffusion. This requires that the drug-delivery device have at least one barrier or wall of biologically acceptable ethylene-vinyl acetate copolymer through which the drug will pass by diffusion. Various forms of the invention are included within this framework. Thus, the device of the invention can have a single ethylene-vinyl acetate copolymer membrane on one surface thereof and through which the drug will pass by diffusion. One form of this embodiment is illustrated in FIG. 3, a detailed description of which is presented later in the specification. In another embodiment of the invention, the device is a biologically acceptable container, with walls of ethylene-vinyl acetate copolymer, and the drug in the interior thereof; see FIG. 1 for example. In this form of the invention, drug alone can be within the interior reservoir of the device or the drug can be dispersed in a liquid, semi-solid, or solid matrix and the matrix enclosed within the ethylene-vinyl acetate copolymer barrier. In each of these embodiments, passage of the drug diffusion through the ethylene-vinyl acetate copolymer is the rate controlling step for drug administration. For further details of such a drug-delivery device in which the drug is dispersed throughout a solid matrix enclosed within a barrier through which drug can pass by diffusion, reference is made to copending application Ser. No. 42,786, filed June 2, 1970 and now U.S. Pat. No. 3,854,480 issued on Dec. 17, 1974 for an invention of Alejandro Zaffaroni assigned to the assignee of this invention. The disclosure of that co-pending Application is relied upon and incorporated herein by reference. In another embodiment of the invention (as in FIG. 2), the drug 12 is distributed throughout a matrix, which matrix in this embodiment is reservoir 12a, of ethylene-vinyl acetate copolymer 11. Preferably, solid particles or a liquid form of the drug are used, although the drug can be in solution in the polymeric matrix.

Drug-delivery devices of the invention can take a wide variety of shapes and forms for administering the drugs at controlled rates to different areas of the body. Thus, the invention includes external and internal drug-delivery devices such as skin patches, shape retaining buccal patches, sublingual or shaped buccal tablets, peroral dosage forms, implantates for releasing a drug in the tissues of a living organism, pessaries, prosthesis, artificial glands, vaginal or rectal suppositories, cervical rings as described in Belgian Patent No. 726,454, troches, drug-dispensing intrauterine devices, ocular inserts as described in U.S. Pat. No. 3,416,530, and pre-shaped drug delivery devices for administering a drug in a body cavity. In each instance, the drug-delivery device has an ethylene-vinyl acetate copolymer barrier for release of the drug by diffusion at a controlled rate and it is of appropriate known shape for implantation in the desired body tissues, cavities or the like, respectively, or for application to a particular body internal or external area.

For example, as illustrated in FIG. 3, the drug-delivery device 10 of the invention can be comprised of a film 11 of ethylene-vinyl acetate copolymer on one face surface of a reservoir 12a containing drug 12. The reservoir is bounded by side walls 13 and top surface wall 14 all of which preferably are impermeable to passage of drug 12. About the perimeter of film 11 is a coating of a pressure-sensitive adhesive 15. This drug-delivery device is especially adapted to apply drug to the skin or buccal mucosa by diffusion through film 11 at a predetermined rate.

One especially important use of the invention is in drug dispensing intrauterine devices for controlling fertility. The reason for this is that it has unexpectedly been found that ethylene-vinyl acetate copolymers provide excellent diffusion barriers for the controlled release of progestational agents, such as progesterone, over a prolonged period of time. Such devices incorporate within their interior a progestational agent, such as progesterone, which is released by diffusion through the ethylene-vinyl acetate copolymer walls of the device. The intrauterine contraceptive device is of appropriate shape for comfortable insertion and retention in the uterus. For example, the device can be in the form of a Lippe's Loop in U.S. Pat. No. 3,250,271, Shamrock in U.S. Pat. No. 3,077,879, Birnberg Bow in U.S. Pat. No. 3,319,625, and the like. As illustrated in FIG. 4, the drug-delivery device 10 of the invention is in the form of an acceptable intrauterine device which in use is disposed within lumen 16 of a uterus schematically represented as being defined by sidewalls 17, top wall 18, and cervix 19. By slow diffusion of an anti-fertility agent such as a progestational agent through the ethylene-vinyl acetate copolymer walls of the intrauterine device, fertility can be controlled for long periods of time, for example up to one year or longer.

FIG. 5 illustrates another important use of the invention, in eye medication dispensing devices. Such devices are flexible bodies of ethylene-vinyl acetate copolymer containing an ophthalmic drug, such as pilocarpine, which is dispensed to the eye by diffusion through the copolymer. The device is adapted for insertion in the cul-de-sac of the conjunctiva between the sclera of the eyeball and the lid, to be held in place against the eyeball by the pressure of the lid. As illustrated in FIG. 5, the device 10 of the invention can have ethylene-vinyl acetate copolymer walls 11 surrounding a reservoir 12a containing an ophthalmic drug 12. In use, drug 12 is dispensed to eyeball 20 by diffusion through ethylene-vinyl acetate copolymer walls 11. Device 10 is illustrated as being placed in lower cul-de-sac 21 of the conjunctiva between the sclera of the eyeball and the lower lid 22. Alternatively, device 10 can be placed in upper cul-de-sac 23 of the conjunctiva between the sclera of the eyeball and the upper eyelid 24. In either case, it is held in place against the eyeball by the pressure of the lid. For further details on these eye medication dispensing devices, reference is made to U.S. Pat. No. 3,416,530 and co-pending patent application Ser. No. 831,761 filed June 9, 1969 now U.S. Pat. No. 3,618,604, and assigned to the assignee of this invention. The disclosure of that co-pending application is relied upon and incorporated herein by reference. One important advantage in using ethylene-vinyl acetate copolymers in such eye medication dispensing devices is that precise control over the rate of release of ophthalmic drugs, especially pilocarpine, is obtained, with the drug being released at a therapeutically effective rate.

Ethylene-vinyl acetate copolymers are well known commercially available materials. Exemplary techniques for their preparation are described in U.S. Pat. Nos. 2,200,429 and 2,396,785. In its broadest aspects, the present invention contemplates use of ethylene-vinyl acetate copolymers having a vinyl acetate content of about 4 to 80% by weight of the total and a melt index of about 0.1 to 1000 grams per ten minutes. Melt index is the number of grams of polymer which can be forced through a standard cylindrical orifice under a standard pressure at a standard temperature and thus is inversely related to a molecular weight. As used in this specification and the appended clams, melt index is as determined in accordance with standard ASTM D 1238–65T condition E practice. Preferably, the ethylene-vinyl acetate copolymer has a vinyl acetate content of about 4 to 50% by weight, a melt index of about 0.5 to 250 grams per ten minutes, a density having a range of about 0.920 to 0.980, and a frequency of acetoxy groups on the polyethylene backbond of 1/150 to ⅛. More preferably, the polymer has a vinyl acetate content of 4 to 40% by weight and a melt index of about 0.5 to 25 grams per ten minutes. Moreover, it has been surprisingly found that the absolute release rate of drug through the ethylenevinyl acetate copolymer barrier can be varied and accurately controlled by selecting a copolymer having the frequency of acetoxy group with the range set forth above.

The ethylene-vinyl acetate copolymer, which acts as the rate controlling barrier, is permeable to drugs, to permit passage of the drug by diffusion through the polymer at a relatively low rate. Normally, the rate of passage of the drug through the polymer is dependent on the solubility of the drug therein, as well as on the thickness of the polymeric barrier. This means that selection of particular ethylene-vinyl acetate copolymer compositions will be dependent on the particular drug to be used. By varying the composition and thickness of the rate controlling barrier, the dosage rate per area of the device can be controlled; for the ethylene-vinyl acetate copolymer acts to meter the flow or diffusion of drug to the exterior of the device. Thus, devices of the same surfaces area can provide different dosage of a drug by varying the characteristics of the ethylene-vinyl acetate copolymer.

In addition to varying the percentage of vinyl acetate in the copolymer and the melt index or molecular weight, the properties of the copolymer can be changed by selectively hydrolyzing its acetate groups to alcohol groups. By converting a portion of the vinyl acetate units of the polymer to vinyl alcohol units, the polymer is rendered more hydrophilic and the rate of passage of relatively hydrophilic drug molecules is increased. The percentage of vinyl acetate units hydrolyzed to vinyl alcohol units can vary widely but typically from about 20 to 60% are converted. This partial hydrolysis is a well known procedure and can be accomplished under standard conditions well known in themselves. Exemplary hydrolysis procedures are set forth in U.S. Pat. Nos. 2,386,347; 2,399,653; 3,386,978; 3,494,908; and the like.

Permeability of the copolymer of drugs by diffusion also can be varied by incorporating fillers into the copolymer. Typical fillers that can be employed in practice of the invention are silica, clay, barytes, carbon black, lithopone, zinc oxide, etc. It should be realized that use of many of these fillers will affect the melt index of the copolymer. However, when melt index is used herein to define the copolymer it is used as a measure of molecular weight and refers to the melt index of the particular copolymer composition without any filler present. Additionally, in those instances where the rate of release of drug is less than a preselected rate, the drug can be converted to known derivatives that have a greater permeability of drug through the membrane to increase the rate of release. Also, where the rate of drug diffusion is too slow, the rate can easily be increased by using drug delivery devices as embodied in FIG. 2.

Selection of the particular ethylene-vinyl acetate copolymer is governed in large part by the drug to be incorporated in the device, as well as by the desired rate of release of the drug. Those skilled in the art can readily determine the rate of diffusion of drugs through these copolymers and select suitable combinations of copolymer and drug for particular applications. Various techniques can be used to determine the permeability of the copolymers to different drugs. One that has been found to be eminently well suited is to cast or hot press a film of the copolymer to a thickness in the range of 2 to 60 mils. The film is used as a barrier between a rapidly stirred (e.g. 150 r.p.m.) saturated solution of the drug and a rapidly stirred solvent bath, both maintained at constant temperature (typically 37° C). Samples are periodically withdrawn from the solvent bath and analyzed for drug concentration. By plotting drug concentration in the solvent bath versus time, the permeability constant P of the film is determined by the Fick's First Law of Diffusion.

$$\text{Slope of plot} = (Q_1 - Q_2)/(t_1 - t_2) = P(AC/h)$$

wherein
$Q_1$ = cumulative amount of drug in solvent in micrograms at $t_1$
$Q_2$ = cumulative amount of drug in solvent in micrograms at $t_2$
$t_1$ = elapsed time to first sample, i.e., $Q_1$
$t_2$ = elapsed time to second sample, i.e., $Q_2$
$A$ = area of film in cm$^2$
$C$ = initial concentration of drug in saturated solution at $t$
$h$ = thickness of film in cm By determining the slope of the plot, i.e., $(Q_1 - Q_2)/(t_1 - t_2)$ and solving the equation using the known or measured values of A, C, and $h$, the permeability P constant in cm$^2$/time of the film for a given drug is readily determined. Of course, this permeability constant is an inherent characteristic of a copolymer of particular composition and melt index and is unchanged whether the material is used as a matrix or as a film wall. The procedures used to determined the rate of drug release through the ethylene-vinyl acetate copolymer can easily be ascertained by standard techniques known to the art as recorded in *J. Pharm. Sci.*, Vol. 52, pages 1145 to 1149, 1963; *ibid* Vol. 53, pages 798 to 802, 1964; *ibid* Vol. 54, pages 1459 to 1464, 1965; *ibid* Vol. 55, page 840 to 843 and 1224 to 1239, 1966; *Encyl. Polymer. Sci. Technol.*, Vol. 5 and 9, pages 65 to 82 and 794 to 807, 1968; the references cited therein, and the like.

The rate of solubilization, or the rate at which drug will go into solution or dissolve in a vehicle confined within the reservoir is quantitatively governed by known physico-chemical principles. For an example, a drug particle dispersed in a vehicle is surrounded by a thin layer of vehicle having a finite thickness l in cm. This layer is considered as an integral part of the drug and it is characteristically referred to as the "stagnant layer." The stagnant layer remains a part of the surface of the drug, moving wherever the drug moves. Using Fick's First Law of Diffusion, the rate of solution is the rate at which a dissolved drug diffuses through the stagnant layer for supplying drug to the drug device's reservoir's inner wall. The driving force behind the movement of the drug through the stagnant layer is the difference in concentration of the drug, $C_1$, in the stagnant layer at the surface of the drug and the concentration $C_2$ on the farthest side of the stagnant layer. The difference in concentration $C_1 - C_2$ determines the rate at which drug is solubilized in the vehicle. Hence, if the vehicle on the farthest side contains its optimum concentration because of a low release by the drug release rate controlling wall, the rate of solubilization of new drug will be low. Correspondingly; as drug leaves the vehicle new drug is solubilized to establish a steady state within the vehicle.

The rate of diffusion of a drug in the vehicle comprising the reservoir is broadly determined by measuring the rate of a drug transferred from one chamber through a sintered glass filter of known pore size and thickness into another chamber and calculating from the obtained data the drug transfer rate. The method is carried out by adding to a first conical flask equipped with a ground glass stopper and a stirring bar, a measured amount of vehicle and simultaneously, the drug in the same vehicle is added to a second conical flask while keeping the level of the vehicle in the two flasks the same. Next, the flasks are stirred, and samples drawn at various time intervals for analysis. The measured rate of drug transport through the sintered glass filter, and the concentration difference of the drug in the two flasks is then calculated. These procedures are known to the art in *Proc. Roy. Sci. London, Ser. A. Vol.* 148, page 1935; *J. Pharm. Sci., Vol.* 55, pages 1224 to 1229, 1966; and references cited therein. The diffusion coefficient of a drug can also be experimentally determined by using the above apparatus or similar apparatus and procedures as described in *Duffusion in Solids, Liquids and Gases,* by W. Jost, Chapter XI, pages 436 to 488, 1960, Revised Edition, Academic Press Inc., New York.

The solubility of a drug in the drug release rate controlling ethylene-vinyl acetate copolymer material comprising the wall of a drug delivery device broadly is determined by preparing a satuated solution of a given drug and ascertaining, by analysis, the amount present in a definite area of the copolymer material. For example, the solubility of the drug in the wall is determined by first equilibrating the wall material with a saturated solution of the drug at a known temperature, for example 37° C, or with a pure liquid drug, if the drug is a liquid at 37° C. Next, drug is desorbed from the saturated wall material with a suitable solvent for the drug. The resultant solution for the drug then is analyzed by standard techniques such as ultraviolet, visible spectrophotometry, refractive index, polarography, electrical conductivity and the like, and calculating from the data the concentration, or solubility of the drug in the material.

The solubility of a drug in a vehicle can be determined by various art known techniques. One method consists in preparing a vehicle, of the given drug and ascertaining by analysis the amount of drug present in a definite quantity of the vehicle. A simple apparatus for this purpose consists of a test tube of medium size fastened upright in a water bath maintained at constant temperature. The vehicle and drug are placed in the tube and stirred by means of a motor driven rotating glass spiral. After a given period of stirring, a definite weight of the vehicle is analyzed and the stirring continued for an additional period of time. If the analysis shows no increase of dissolved substance after the second period of stirring, the results are taken as the degree of solubility of the drug in the vehicle. Numerous other methods are available for the determination of the degree of solubility of a drug in a vehicle. Typical methods used for the measurement of solubility are chemical analysis, measurement of density, refractive index, electrical conductivity, and the like. Details of various methods for determining solubilities are described in United States Public Health Service Bulletin No. 67 of the Hygienic Laboratory; *Encyclopedia of Science and Technology, Vol.* 12, pages 542 to 556, 1971, published by McGraw-Hill, Inc.; *Encyclopaedic Dictionary of Physics, Vol.* 6, pages 545 to 557, 1962, published by Pergamon Press, Inc; and the like.

Also according to Fick's Law, the rate of drug solution is directly proportional to the area of the drug, A in $cm^2$, as exposed to vehicle and inversely proportional to the length of the path through which the dissolved drug molecule must diffuse. Then, the rate of solution of the drug is given by $$R = DA/l(C_1 - C_2)$$

wherein R is the rate of solution, D is a proportionality constant called diffusion coefficient in $cm^2/sec$, and $C_1$, $C_2$ and $l$ are as previously defined. See *Remington Pharmaceutical Science,* 14the Ed., pages 246 to 269, 1970, published by Mack Publishing Company.

In practicing the invention, one can employ any drug used to treat the body and capable of diffusing through an ethylene-vinyl acetate copolymer at a therapetucially effective rate. Suitable drugs for use in therapy with the drug-delivery device of the invention include, without limitation, drugs that produce a physiologically or pharmacologically localized or systemic effect or effect in mammals including human and primates, avians such as chicken and turkeys; valuable domestic household, sport or farm animals such as horses, dogs, cats, cattle, sheep and the like; or for administering to laboratory animals such as mice, monkeys, rats, guinea pigs; and the like. The active drugs that can be administered by the novel drug delivery device of the invention include, without limitation:

1. Anti-infectives, such as antibiotics, including penicillin, tetracycline, chloramphenicol, sulfacetamide, sulfamethazine, sulfadiazine, sulfamerazine, sulfamethizole and sulfisoxazole; antivirals, including idoxuridine; and other anti-infectives including nitrofurazone and the like;

2. Anti-allergenics such as antazoline, methapyrilene, chlorpheniramine, pyrilamine and prophenypridamine;

3. Anti-inflammatories such as hydrocortisone, cortisone, dexamethasone, fluocinolone, triamcinolone, medrysone, prednisolone, and the like;

4. Decongestants such as phenylephrine, naphazoline, and tetrahydrazoline;

5. Miotics and antichlolinesterases such as pilocarpine, carbachol, and the like;

6. Mydriatics such as atropine, cyclopentolate, homatorpine, scopolamine, tropicamide, eucatropine and hydroxyamphetamine;

7. Sympathomimetics such as epinephrine;

8. Sedatives and Hypnotics such as chloral, pentabarbital, phenobarbital, secobarbital, codeine, (α-bromoisovaleryl) urea, and carbromal;

9. Psychic Energizers such as 3-(2-aminopropyl) indole, 3-(2-aminobutyl) indole, and the like;

10. Tranquilizers such as reserpine, chlorpromazine, and thiopropazate;

11. Androgenic steroids such as methyltestosterone and fluoxymesterone;

12. Estrogens such as estrone, 17β-estradiol, ethinyl estradiol, and diethyl stilbesterol;

13. Progestational agents, including progestogen and progestins, such as progesterone, 19-nor-progesterone, norethindrone, megestrol, melengestrol, chloromadinone, ethisterone, medroxyprogesterone, norethynodrel and 17α-hydroxy-progesterone;

14. Humoral agents such as the prostaglandins, for example $PGE_1$, $PGE_2$, and $PGF_{2\alpha}$;

15. Antipyretics such as aspirin, salicylamide, and the like;

16. Antispasmodics such as atropine, methantheline, papaverine, and methscopolamine;

17. Anti-malarials such as the 4-aminoquinolines, α-aminoquinolines, chloroquine, and pyrimethamine;

18. Antihistamines such as diphenhydramine, dimenhydrinate, tripelennamine, perphenazine, and chloropenazine;

19. Cardioactive agents such as benzydroflumethiazide, flumethiazide, chlorothiazide, and aminotrate; and 20. Nutritional agents such as essential amino acids and essential fats. Other drugs having the same or different physiological activity as those recited above can be employed in drug-delivery devices within the scope of the present invention.

Drugs, contained in the reservoir, can be in different forms, such as uncharged molecules, components of molecular complex or non-irritating, pharmacologically acceptable derivatives thereof. For simple derivatives of the drugs such as pharmaceutically acceptable ethers, esters, amides, and the like which have desirable retention and release characteristics but which are easily hydrolyzed by body pH, enzymes to active forms, and the like can be employed.

The dosage unit amount for conventional beneficial drugs as set forth herein, in the accompanying disclosure and examples, is also known to the art in standard reference books such as *Remington's Pharmaceutical Science,* Fourteenth Edition, Part IV, 1970, published by Mack Publishing Col, Easton, Penn.

The amount of drug incorporated in the drug-delivery device varies depending on the particular drug, the desired therapeutic effect, and the time span for which the device provides therapy. Since a variety of devices in a variety of sizes and shapes are intended to provide dosage regimes for therapy for variety of maladies, there is not critical upper limit on the amount of drug incorporated in the device. The lower limit too will depend on the activity of the drug and the time span of its release from the device. Thus, it is not practical to define a range for the therapeutically effective amount of drug to be incorporated in or released by the device. However, the amount of drug present in the reservoir is generally non-limited and it is an amount equal to or larger than the amount of drug that on its release from the device is effective for bringing about the drug's physiological or pharmacological local or systemic effects. For example, the amount of drug present in the reservoir of a drug-delivery device when the device is used for a period of time to achieve local or systemic effect is for various drugs, such as 11-desmethoxyreserpine about 5 to 40 mg in the reservoir; for acetophenazine an amount in the reservoir of 100 to 200 mg; for hydrocortisone about 2 to 10 mg in the reservoir; for progesterone a reservoir amount of 6.0 to 300 mg; for pilocarpine a reservoir amount of 2 to 10 mg; about 160 to 250 mg of butabarbital in the reservoir; about 150 to 170 mg of chlorodiazepoxide; from 0.5 to 0.75 gm of methsuximide; from 0.7 to 1.0 gm of ethosuximide; from 20 to 40 mg of hydrolazine; about 50 to 100 mg of totazoline; and the like. Generally, the drug delivery devices made according to the invention can contain from about 250 nanograms to 5 grams of drug for releasing it at a controlled rate of from about 25 nanograms to about 25 grams of drug or larger amounts per day. Of course, other devices containing different amounts of drug for use for different time periods such as week, month and year are also readily made by the invention.

It will be appreciated by those versed in the art that the unique drug delivery device of this invention can provide for the programmed delivery of drug at a rate of delivery characterized by a zero order time dependence for prolonged period of time; and, that the device therefore lends itself to administering an effective amount of drug needed for a therapeutic effect while essentially avoiding the presence of excessive amount of drug at the needed biological site. By a prolonged period of time is meant, as used herein, periods that embrace the time needed for a fast acting drug to effect its end up to periods that embrace the continual, uninterrupted, repititious time of a long term drug delivery device. For example, the prolonged time can be one hour or more for drugs, like local anesthetics, analgesics, prostaglandins or the like, that are effective in nanogram and milligram amounts, or the like, to three years or longer for steroids released within the uterine cavity. Other examples include wherein the amount of drug in the reservoir can be 100 to 300 mg of thiopropzate for releasing 15 to 30 mg over a 24 hour period; 2 to 10 mg in the reservoir of pilocarpine for a release of 8 to 25 μg per hour; 2 to 10 mg of hydrocortisone for releasing 10 μg/hr.; 100 to 200 mg of papaverine in the reservoir for a release 30 to 75 mg over a 24 hour period; 15 to 25 mg of tranylcypromane for a release of 10 to 15 mg as the standard dose; prostaglandins for example $PGE_1$, $PGE_2$, $PGA_1$, $PGF_{2\alpha}$ in amounts of 0.5 mg to 20 mg for release of intrauterine drug to a mature female mammal at the rate of 10 ng to 100 ng and the like; for progestational, progestogen, or progesterone the administration in the uterus of 10 to 600 μg per day for release for 1 year to 3 years as an anti-fertility agent in a mature, child-bearing woman weighing 40 kg to 85 kg; an oral device administering 300 mg to 600 mg per day of analgesic acetaminophen to a 60 to 70 kg adult male; and the like.

Drug-delivery devices of the invention are easily fabricated. When the system is in the form of a matrix with drug distributed therethrough, particles of the drug can be mixed with the ethylene-vinyl acetate copylmer, which can be in the solid, semi-solid, or liquid form at the time, and distributed therethrough by ball-milling, callendering, stirring, shaking or the like. Where the drug is chemically compatible with the monomers used to form the ethylene-vinly acetate copolymer, the drug particles can be added at this earlier stage and the ethylene-vinyl acetate matrix formed in situ. The matrix, however, made and having the drug particles distributed therethrough, can then be formed to a solid shape by molding, casting, pressing, extruding, drawing or like processes. Thereafter, the matrix can be cross-linked, if desired, for example, by use of irradiation. Alternatively, the ethylene-vinyl acetate copolymer matrix can be formed to the desired shape and placed in a bath of the drug or of a solvent solution of the drug which then diffuses into the matrix to provide the drug-delivery device. When the drug-delivery device is a sealed container with walls of ethylene-vinyl acetate and the drug in an interior reservoir, the container can be fabricated in many ways. Preformed hollow shapes of ethylene-vinyl acetate, copolymer such as tubing, can be filled with drug, alone or dispersed in a suitable vehicle, and the ends sealed with plugs or by heat to form the final drug-delivery device. Alternatively, the drug can be laminated between ethylene-vinyl acetate copolymer sheets which can be sealed together with adhesive or by heat. Other encapsulation, bonding, and coating techniques conventionally used in the art can be employed. The ability to shape ethylene-vinyl acetate copolymers into tubes, rods, disks, films, rings and other highly reproducible shapes of controllable composition results in ready fabrication of devices with closely controlled characteristics and overcomes a significant disadvantage of previously described devices based on silicone rubber polymers and other presently known polymers. Other standard procedures, as described in *Modern Plastics Encyclopedia, Vol.* 46, pages 62 to 70, 1969, published by McGraw Hill Co. well known to those skilled in the art can be used to fabricate the drug delivery device of the invention.

In addition to its ease of fabrication, the drug-delivery device of the invention offers other important advantages. One of these is that diffusion of drugs, such as progesterone, through ethylene-vinyl acetate copolymers proceeds at a lower rate than through silicone rubber and other prior art polymers. This is important because it ensures that the rate of drug administration is controlled by diffusion through the polymer rather than by clearance from the surface of the device. In addition, ethylene-vinyl acetate copolymers are not known to absorb lipoidal materials at the same rate from the body, as do silicone rubber membranes and some other polymers, and therefore the characteristics of the rate controlling membrane do not vary with time. This permits use of drug-delivery devices of the invention for long term therapeutic programs, for example, in hormone releasing intrauterine devices or in implantates. Use of silicone rubber and the like as the rate controlling barrier in such long term dosage forms has not generally been successful. Another added advantage of the present invention is that ethylene-vinyl acetate compolymer seemingly does not give rise to unwanted effects when in contact with biological media.

The reservoir of the drug-delivery device in one embodiment of the invention is a drug matrix that contacts the inner surface of the drug release rate controlling ethylene-vinyl acetate copolymer wall and supplies drug thereto. The reservoir is comprised of a liquid, semi-solid or solid matrix containing drug, and it is a material that is permeable to the passage of drug by diffusion. The matrix can be an organic, inorganic, naturally occurring or synthetic material. Examples of matrix are gelatin, starches, carbohydrates, Irish moss, hydrophilic hydrogels of esters of acrylic acid, modified collagen and like materials. Also, other commercially available matrixes permeable to the passage of drug but at a higher rate of passage than through the wall of the device are suitable for the reservoir of the device. Representative matrixes are set forth in *Remington's Pharmaceutical Science,* pages 246 to 269, 1338 to 1390 and 1627 to 1979, 1970, published by Mack Publishing Company, Easton, Penn.

The following examples are merely illustrative of the present invention and they should not be considered as limiting the scope of the invention in any way, as these examples and other equivalents thereof will become apparent to those versed in the art in the light of the present disclosure, drawings and the accompanying claims.

EXAMPLE 1

Milled crystals of progesterone (60 milligrams) are placed within a tube 1.5 cm long, having an inside diameter of 0.125 inch and an outside diameter of 0.157 inch and formed from an ethylene-vinyl acetate copolymer essentially insoluble in biological fluids and having a vinyl acetate content of 28% by weight and a melt index of 4 grams per ten minutes. The tube ends are heat sealed and the dosage unit used for conception control by attachment to an intrauterine device for example, a Lippe's Loop and inserted into the uterine lumen through the cervix. The device controls fertility by releasing 56 micrograms of progesterone per day to the uterine cavity of an adult woman.

EXAMPLE 2

Milled crystals of medroxyprogesterone acetate (980 milligrams) are placed within a tube 23 cm long, having an inside diameter of 0.125 inch and an outside diameter of 0.157 inch and having walls formed of biologically acceptable, ethylene-vinyl acetate copolymer having a vinyl acetate content of 40% by weight and a melt index of 15 grams per ten minutes. The filled tube is bent to a ring having a circumference of 23 cm and the ends heat sealed together. The device is placed in the vagina at the mouth of the cervix and regulates fertility by release of medroxyprogesterone acetate at a slow rate intravaginally for a prolonged period of time.

EXAMPLE 3

Milled crystals of hydrocortisone (800 milligrams) are placed on a film of ethylene-vinyl acetate copolymer having a thickness of 4 mils, a face surface area of 4 cm$^2$, and formed from a copolymer having a vinyl acetate content of 16% by weight and a melt index of 2.5 grams per ten minutes. The hydrocortisone bearing surface of the film is overlaid with a polyethyleneterephthalate sheet of the same dimensions which is heat sealed at its edges to the ethylene-vinyl acetate film. A strip of pressure-sensitive adhesive (70 parts of 95:5 copolymer of isoamyl acrylate and acrylic acid, 5 parts polyvinylethylether with reduced viscosity of 0.3, 1 part castor oil and 4 parts polyethylene-glycol-400) having a width of 2 mm is printed on the face surface of the ethylene-vinyl acetate film about the perimeter thereof. When applied to the skin, hydrocortisone diffuses through the ethylene-vinyl acetate copolymer sheet, is absorbed by the skin, and is effective to treat various dermatitis conditions.

EXAMPLE 4

Milled crystals of diethylstilbestrol (950 milligrams) are mixed with an ethylene-vinyl acetate copolymer having a vinyl acetate content of 22% by weight and a melt index of 14 grams per ten minutes. The drug-copolymer mixture is ball milled for 20 minutes to provide a uniform distribution of the throughout the polymeric carrier. Thereafter, the resulting mixture is shaped in the form of a cylinder having a length of 2 cm and a circumference of 0.12 cm. When implanted in the ear of beef cattle, the implantate releases an effective amount of diethylstilbestrol to induce weight gain in the farm animal.

EXAMPLE 5

Pilocarpine oil (200 milligrams) is placed between two films of ethylene-vinyl acetate copolymer each having a thickness of 0.004 inch and formed from an ethylene-vinyl acetate copolymer with a vinyl acetate content of 40% by weight and a melt index of 22 grams per ten minutes. Ellipsoidal ocular inserts having a length of 1.3 cm, a width at their widest point of 4 mm, and a thickness of 0.5 mm, are heat stamped from the assemblage, with each such insert containing 2 milligrams of pilocarpine. These ocular inserts can be inserted and retained in the cul-de-sac of the conjunctiva between the sclera of the eyeball and the lid, and, when in place, will release a therapeutically effective amount of pilocarpine to control glaucoma to an adult human over a period of 24 hours.

EXAMPLE 6

An intrauterine anti-fertility dispensing device is shaped like a triangle with an opening at the vertex of two of the legs. The triangle is formed of a release rate controlling wall permeable to the passage of an anti-fertility agent and surrounding a reservoir containing a carrier and the agent. The triangle is made as follows: first, a carrier containing progesterone is injected into a length of biologically acceptable, nonerodible, ethylene-vinyl acetate copolymer. The ends of the tubing are heat sealed and the tubing is then formed into a triangle device in a heated mold. The device releases intrauterine 90 to 100 micrograms of progesterone per day to a 40 to 80 kg woman.

In summary, it will be readily appreciated that the present invention contributes to the art unobvious drug delivery devices having wide and practical application by the invention's use of ethylene-vinyl acetate copolymer. As noted supra, it has now been found that ethylene-vinyl acetate copolymer can be used for the controlled release of many drugs. In contrast, highly crystalline materials such as polyethylene or materials such as partially hydrolyzed polyvinyl acetate having a profusion of side groups, do not lend themselves to use in like environments. And, while the invention has been described and pointed out in detail and with reference to operative embodiments thereof, it will be understood that those skilled in the art will appreciate that various changes, modifications, substitutions and omissions can be made without departing from the spirit of the invention. It is intended, therefore, that the invention embrace these equivalents within the scope of the claims which follow.

We claim:

1. An ocular therapeutic system for the controlled release of drug comprising a flexible body formed of a polymeric material permeable to the passage of drug by diffusion and containing a drug capable of diffusing through the material at a therapeutically effective rate, the body shaped, sized and adapted for comfortable insertion and retention in the cul-de-sac of the conjuctiva between the sclera of the eyeball and the lid to be held in place against the eyeball by the pressure of the lid, and wherein said polymeric material comprises an ethylene-vinyl acetate copolymer having a vinyl acetate content of about 4 to 80% by weight, and a melt index of about 0.1 to 1000 grams per ten minutes.

2. The ocular system according to claim 1 wherein the drug is an ophthalmic drug.

3. The ocular system according to claim 1 wherein the drug is pilocarpine.

4. An ocular therapeutic system for the controlled release of drug comprising a flexible body formed of a polymeric material permeable to the passage of drug by diffusion and surrounding a drug capable of diffusing through the material at a therapeutically effective rate, the body shaped, sized and adapted for comfortable insertion and retention in the cul-de-sac of the conjunctiva between the sclera of the eyeball and the lid, to be held in place against the eyeball by the pressure of the lid, and wherein said polymeric material comprises an ethylene-vinyl acetate copolymer having a vinyl acetate content of about 4 to 80% by weight, and a melt index of about 0.1 to 1000 grams per ten minutes.

5. The ocular system according to claim 4 wherein the body is a container with drug contained therein.

6. The ocular system according to claim 4 wherein the drug is an ophthalmic drug.

7. The ocular system according to claim 4 wherein the drug is pilocarpine.

8. An ocular therapeutic system for the controlled and continuous administration of drug to the eye of a warm blooded animal comprising a body formed of a polymeric material permeable to the passage of drug by diffusion and surrounding a drug capable of diffusing through the material at a therapeutically effective rate, the body shaped, adapted and sized with a length of 4 to 20 mm, a width of 0.1 to 12 mm and a thickness of 0.1 to 4 mm for insertion and retention in the eye, and wherein the material comprises an ethylene-vinyl acetate copolymer having a vinyl acetate content of about 4 to 80% by weight and melt index of about 0.1 to 1000 grams per ten minutes, with the copolymer when the system is in the eye administering drug to the eye at a controlled rate over a prolonged period of time.

9. The ocular system according to claim 8 wherein the body is a container and the drug is contained therein.

10. The ocular system according to claim 8 wherein the copolymer surrounds a reservoir containing an ophthalmic drug.

11. The ocular system according to claim 8 wherein the drug is pilocarpine.

12. An ocular therapeutic system for the controlled administration of drug to the eye comprising a body formed of a drug release rate controlling ethylene-vinyl acetate copolymer permeable to the passage of drug by diffusion and containing a dosage amount of a drug capable of diffusing through the copolymer, said body shaped, adapted and sized for comfortable insertion and placement in the eye, and wherein the body when in the eye administers a therapeutically effective amount of drug by the drug dissolving in and passing through the copolymer at a controlled rate over a prolonged period of time.

13. The ocular system according to claim 12 wherein the copolymer has a vinyl acetate content of 4 to 50% by weight, a melt index of 0.5 to 250 grams per 10 minutes, a density of 0.920 to 0.980, and a frequency of acetoxy groups on the ethylene backbone of 1/150 to ½.

14. The ocular system according to claim 12 wherein the drug is an ophthalmic drug.

15. The ocular system according to claim 12 wherein the drug is pilocarpine.

16. An ocular therapeutic system for administering drug to the eye comprising a body shaped and sized for comfortable insertion and retention in the eye, the body formed of a drug release rate controlling ethylene-vinyl acetate copolymer having a vinyl acetate content of 4 to 80% by weight, permeable to the passage of drug by diffusion and surrounding a drug capable of diffusing therethrough, and wherein said body when in the eye administers a therapeutically effective amount of drug by passage through the copolymer at a controlled rate over a prolonged period of time.

17. The ocular system for administering drug to the eye according to claim 16 wherein the copolymer has a melt index of 0.1 to 1000 grams per 10 minutes and the drug is an ophthalmic drug.

18. The ocular system according to claim 16 wherein the body is a container with the drug contained in the reservoir thereof.

19. The ocular system according to claim 16 wherein the drug is pilocarpine.

* * * * *